United States Patent
Smith et al.

(10) Patent No.: US 11,590,068 B2
(45) Date of Patent: Feb. 28, 2023

(54) PERSONAL CARE PRODUCTS

(71) Applicant: DAMIVA INC., Toronto (CA)

(72) Inventors: Gardiner F. H. Smith, Elizabeth, WV (US); Chia Chia Sun, Toronto (CA)

(73) Assignee: DAMIVA INC., Toronto (CA)

( * ) Notice: Subject to any disclaimer, the term of this patent is extended or adjusted under 35 U.S.C. 154(b) by 175 days.

(21) Appl. No.: 16/604,473

(22) PCT Filed: Apr. 10, 2018

(86) PCT No.: PCT/US2018/026949
§ 371 (c)(1),
(2) Date: Oct. 10, 2019

(87) PCT Pub. No.: WO2018/191296
PCT Pub. Date: Oct. 18, 2018

(65) Prior Publication Data
US 2021/0128443 A1    May 6, 2021

Related U.S. Application Data

(60) Provisional application No. 62/483,785, filed on Apr. 10, 2017.

(51) Int. Cl.
| | | |
|---|---|---|
| A61K 8/92 | (2006.01) | |
| A61K 8/04 | (2006.01) | |
| A61K 8/60 | (2006.01) | |
| A61K 8/73 | (2006.01) | |
| A61K 8/9789 | (2017.01) | |
| A61K 9/00 | (2006.01) | |
| A61K 9/02 | (2006.01) | |
| A61K 36/185 | (2006.01) | |
| A61Q 19/00 | (2006.01) | |

(52) U.S. Cl.
CPC ............... *A61K 8/922* (2013.01); *A61K 8/60* (2013.01); *A61K 8/735* (2013.01); *A61K 8/9789* (2017.08); *A61K 9/0034* (2013.01); *A61K 9/0036* (2013.01); *A61K 9/02* (2013.01); *A61K 36/185* (2013.01); *A61Q 19/001* (2013.01); *A61Q 19/005* (2013.01); *A61Q 19/007* (2013.01); *A61K 8/04* (2013.01); *A61K 2800/30* (2013.01); *A61K 2800/87* (2013.01)

(58) Field of Classification Search
None
See application file for complete search history.

(56) References Cited

U.S. PATENT DOCUMENTS

| | | |
|---|---|---|
| 2003/0157050 A1 | 8/2003 | Ambrosen et al. |
| 2005/0085653 A1* | 4/2005 | Garro ............... C11C 1/005 |
| | | 554/174 |
| 2009/0068128 A1 | 3/2009 | Waddington |
| 2013/0095196 A1 | 4/2013 | Raymond-Coblantz |
| 2015/0297501 A1 | 10/2015 | Constantine et al. |
| 2018/0148665 A1* | 5/2018 | Goodrich ........... A23D 9/04 |

FOREIGN PATENT DOCUMENTS

| | | |
|---|---|---|
| CN | 105640804 A | 6/2016 |
| RU | 2308963 C2 | 10/2007 |

OTHER PUBLICATIONS

Product information sheet obtained from the website:https://dailymed.nlm.nih.gov/dailymed/fda/fdaDrugXsl.cfm?setid=7f4a11c3-95bf-419b-8460-ea9d946fc724&type=display (obtained from Google textserach) (Year: 2014).*
Larmo et al., "Effects of sea buckthorn oil intake on vaginal atrophy inpostmenopausal women: A randomized, double-blind,placebo-controlled study", Maturitas 79 (2014) 316-321.
Mitchell et al., "Efficacy of Vaginal Estradiol or Vaginal Moisturizer vs Placebo for Treating Postmenopausal Vulvovaginal Symptoms a Randomized Clinical Trial" JAMA Internal Medicine, May 2018, vol. 178, No. 5, 681-690.
PCT/US2018/026949 International Search Report.
PCT/US2018/026949 Written Opinion.

* cited by examiner

*Primary Examiner* — Sin J Lee
(74) *Attorney, Agent, or Firm* — Venable LLP; Keith G. Haddaway

(57) ABSTRACT

The invention relates to a personal care product for alleviating skin dryness, includes facial skin dryness, breast skin dryness and vulval dryness and for restoring vaginal flora, acidic pH in the vagina, and vaginal health. Embodiments of the personal care product include a formulation including at least about 83 wt. % plant-based glycerides; from about 0.05 wt. % to about 0.15 wt. % sodium hyaluronate; and from about 0.01 wt. % to about 1.5 wt. % sea buckthorn powder. Another embodiment includes a personal care product including at least 55 wt. % plant-based glycerides and from about 20 wt. % to about 42 wt. % sucrose. The personal care product may also include shea olein. The person care product is substantially free of added water, alcohol, synthetic chemical, anti-microbial agent, and synthetic hormone.

17 Claims, No Drawings

PERSONAL CARE PRODUCTS

FIELD OF THE INVENTION

This invention relates to personal care products. More specifically, this invention relates to personal care products for use by women, especially those experiencing hormonal fluctuations or decline. Hormonal fluctuations or decline can be related to, for example, birth control, hormone therapy, menstruation, medications usage, childbirth, cancer treatment, polycystic ovary syndrome, perimenopause or menopause. The personal care products include vaginal suppositories and moisturizers for the face, breast, labia, and vulva.

BACKGROUND

Women's bodies undergo myriad changes through time, from puberty to childbearing years to post-menopause. Hormone in the body fluctuates during these time periods. During hormonal fluctuation, the production of estrogen, testosterone, and progesterone changes. As a result, women may experience symptoms such as: irregular periods, hot flashes, insomnia, night sweats, sleep irregularity, mood changes, vaginal dryness, vaginal pain, urinary urgency, discomfort during sex, fatigue, breast tenderness, low sex drive, confusion, moodiness, and loss of bone density. However, not all women experience all the symptoms to the same degree.

A common problem occurring during hormone fluctuation is tissue dryness. This dryness can occur in skin on any part of the body. However, dryness is a particular problem in delicate and sensitive tissues such as the breasts, the vulva, the vagina, lips and the face.

Although hormonal changes occur throughout life, women experience the greatest hormonal changes during perimenopause and menopause. When a woman misses her period for 12 months consecutively, she has reached menopause. Perimenopause (menopausal transition) is the time period before a woman reaches menopause during which the female body is undergoing a transition in hormone production and other biological functions related to child bearing and loss of fertility. Perimenopause can begin shortly after the prime child bearing years and occurs at a different age for each individual woman. While for most women, perimenopause begin in their 40s, for some, it can happen as early as their late 30s. The average age for women to reach menopause is about 52. Therefore, for some women, perimenopause can last 10 or more years. While many women are familiar with menopause and the biological changes that ensure, most have very little awareness of perimenopause and the changes associated with perimenopause. There is, thus, a continuing need for products that address biological changes of women that occur around and during this significant transition period.

During perimenopause, the production of estrogen, testosterone, and progesterone changes. As a result, women may experience symptoms such as: irregular periods, hot flashes, insomnia, night sweats, sleep irregularity, mood changes, vaginal dryness, vaginal pain, urinary urgency, discomfort during sex, fatigue, breast tenderness, low sex drive, and loss of bone density. However, not all women experience all the symptoms to the same degree.

A common problem occurring during perimenopause is tissue dryness. This dryness can occur in skin on any part of the body. However, dryness during perimenopause is a particular problem in delicate and sensitive tissues such as the breasts, the vulva, the vagina, lips and the face.

A particular underappreciated symptom of perimenopause is vulval dryness. The vulval includes the vaginal lips (labia majora and labia minora), clitoris, vulval vestibule, urinary meatus, vestibular glands and the opening to the vagina. Vulval skin is more sensitive than skin on other parts of the body because it is much thinner. During perimenopause, women often experience vulval dryness, which causes symptoms such as itching, pain, rawness, and painful sex. Although commonly known to occur during menopause, many women are unaware that these are common problems prior to the onset of menopause, i.e. during perimenopause.

Other problem frequent in perimenopause and menopause is the onset of genitourinary syndrome and vaginal atrophy. Genitourinary syndrome, which relates to urgency, dysuria, and recurrent urinary tract infections associated with perimenopause and menopause. Vaginal atrophy (also known as atrophic vaginitis, vulvovaginal atrophy, or urogenital atrophy) is an inflammation of the vagina due to the thinning and shrinking of the vaginal tissues, and the decreased of lubrication. Left unaddressed, vaginal atrophy can lead to pain and discomfort, including vaginal dryness, burning, and discharge; genital itching; burning or urgency with urination; discomfort during and light bleeding after intercourse; decreased vaginal lubrication during sexual activity; shortening and tightening of the vaginal canal; pelvic floor muscle seizure; and atrophy closure of the vagina including scarring and prolapse of an organ through the vagina. Sexual activity is essential to proper exercise, endogenous hormone maintenance, and maintenance of the vaginal track, yet left untreated vaginal dryness can result in painful microabrasions along the entire membrane of the vagina, shrinkage, scarring and closure.

Another specific problem during hormonal fluctuation is breast dryness or tenderness, also known as mastalgia. This can result in discomfort in normal daily activities, including disruption of normal movement, concentration, sleep, and intimacy.

Another specific problem with hormonal fluctuation are the related problems of fatigue and/or lack of sleep. When the ovaries stop producing hormones at significant levels, the adrenal glands attempt to compensate. However, the adrenal glands only produce a small fraction of hormone that the ovaries produced prior to perimenopause and menopause. This reduction of hormone leads to fatigue. Exacerbating this problem is an adrenal response to the increased stress which fatigue can cause, where the adrenal glands consistently produce a rapid and large increase in cortisol, the "fight or flight" hormone. Cortisol spikes often occur in the middle of the night, interrupting sleep and preventing women from getting back to sleep. This condition of sleep interruption typically worsens over time if left unaddressed. Other associates symptoms may include confusion and increased moodiness or mood changes.

Another generalized problem with hormonal fluctuation is the increase in chemical hypersensitivity which accompanies dramatic hormonal decline. When the skin (in particular sensitive areas of the skin like the vaginal, vulva, labia, breasts, nipples, face or lips) comes into contact with a cream or paste based product that contains synthetic chemicals, women experiencing perimenopause have a high potential to feel skin irritation, fatigue, and pain.

To alleviate some of the symptoms of hormonal fluctuation, women have been prescribed low-dose birth control pills to address the change of hormones in their bodies. Others have also used birth control skin patches, vaginal rings, and progesterone injections as hormone treatments. While replacement hormone therapy may alleviate some symptoms, such as hot flashes, sweats, and mood changes, it is less effective in treating dryness, such as skin dryness, breast dryness, vaginal dryness, and vulval dryness, and the concomitant results of dryness, such as skin discomfort, breast sensitization, vaginal pain, and discomfort during sex. Women have also used personal lubricants, body lotions, and petroleum jelly-based products to ease some of these discomforts. However, neither topical hormone therapy nor use of chemical-laden moisturizer gels provides relief of the most bothersome symptoms of women over a 3-month period.

Unfortunately, alternatives such as personal lubricants including water-based, synthetic oil-based, or silicone-based lubricants are undesirable because they contain synthetic chemicals including preservatives and stabilizers. Thus, heightened chemical sensitivity in perimenopausal and menopausal women makes the use of chemical based lubricants detrimental. Additionally, water and alcohol based lubricants dehydrate the skin with medium and long term use, much like bathwater shrives the skin on one's hands due to the concentration gradient across the skin membrane that pulls intracellular fluids out of the skin. Existing personal lubricants and moisturizers were designed to enhance the male experience with short term lack of friction during sexual activities, but in fact deteriorate the skin and mucous membrane of women. Clinical trial has shown that neither a chemical-based moisturizer gel nor a topical vaginal hormone therapy improves symptoms over 3 months. Mitchell C M, Reed S D, Diam S, et al. Efficacy of vaginal estradiol or vaginal moisturizer vs placebo for treating postmenopausal vulvovaginal symptoms: a randomized clinical trial [published online ahead of print Mar. 19, 2018]. JAMA Intern Med. See https://www.ncbi.nlm.nih.gov/pubmed/29554173.

In their quest for natural product based solutions to these universal problems caused by normal aging of the female body, now representing a demographic of nearly half of all women, perimenopausal and menopausal women have attempted to use food type products such as coconut oil or meat lard as lubricants. The issue with the use of these products, besides their not being produced under good manufacturing practices or being contaminant and pathogen tested, is that they do not promote a healthy pH in the vaginal and labial areas. During perimenopause, the vaginal tract goes from acidic to neutral, leading to conditions such as bacterial vaginosis, an infection associated with women where harmful bacteria replaces the normal healthy flora of a women's vaginal tract. In addition to the accompanying pain, odor and fever, these infections typically become chronic and marginally responsive to antibiotic. Women and health care providers often confuse and misdiagnose bacterial vaginosis infections with yeast infection, which typically occurs in women in conjunction with abnormal blood sugar levels. As a result of the misdiagnoses, women are being treated for yeast infection instead of bacterial vaginosis.

Therefore, there is a need for products that specifically target dryness, in particular dryness in sensitive areas for women who are experiencing hormonal fluctuation. More importantly, an all-natural product is advantageous for the vulva to retain moisture and also not cause irritation to the delicate mucous membrane of the vagina. Also, an all-natural product is preferable to bring pH of a women's vaginal area to a healthy acidic level such that the normal vaginal flora may be restored. Furthermore, a product is needed to alleviate facial and breast dryness and can regulate the sleep cycle for women experiencing hormonal fluctuations particularly during perimenopause and menopause.

SUMMARY OF THE INVENTION

The following summary is presented for illustrative purposes and should not serve to limit the scope of the claimed subject matter.

In one embodiment, the present invention is directed to a personal care product, comprising at least about 83 wt. % plant-based glycerides; from about 0.05 wt. % to about 0.15 wt. % sodium hyaluronate; from about 0.01 wt. % to about 1.5 wt. % sea buckthorn powder; and is substantially free of added water or alcohol. In one embodiment, the present invention is directed to a personal care product, comprising at least about 55 wt. % plant-based glycerides; from about 20 wt. % to about 42 wt. % sucrose; and is substantially free of added water or alcohol. In one embodiment, the personal care product is less than about 5 wt. % of added water or alcohol. In one embodiment, the personal care product is substantially free of synthetic chemical, synthetic anti-microbial agent, synthetic preservative, or a synthetic hormone. In one embodiment, the plant-based glyceride comprises cocoa butter; kokum butter; and shea olein. In one embodiment, the plant-based glyceride comprises from about 30 wt. % to about 32 wt. % cocoa butter; from about 14 wt. % to about 16 wt. % kokum butter; and shea olein from about 49 wt. % to about 51 wt. %. In one embodiment, the plant-based glyceride comprises from about 28 wt. % to about 31 wt. % cocoa butter and from about 27 wt. % to about 29 wt. % kokum butter. In one embodiment, the plant-based glyceride is deodorized. In one embodiment, wherein the personal care product has a pH from about 4.3 to about 5 in an aqueous environment, preferably, a pH from about 4.7 to about 5.8 in an aqueous environment, and more preferably from about 5.0 to about 5.5. In one embodiment, the personal care product further comprising from about 0.05 wt. % to about 1.5 wt. % of a natural fragrance oil. In one embodiment, the natural fragrance oil is selected from the group consisting of lavender oil, sandalwood oil, jasmine oil, vanilla oil, gardenia oil, rose oil, and citrus oil. In one embodiment, the personal care product is in a form of cream. In one embodiment, the personal care product is in a form of a vaginal suppository. In one embodiment, the vaginal suppository melts between about 30° C. and about 37° C.

In another embodiment, the present invention is directed to a method for alleviating skin dryness, comprising applying onto dry skin a personal care product of the present invention. In another embodiment, the personal care product is effective for retaining moisture in facial skin, breast skin, or vulva. In another embodiment, the personal care product is effective for retaining moisture in at least one of the vaginal lips (labia majora and labia minora), clitoris, vulval vestibule, urinary meatus, vestibular glands, interior vaginal tract, and the opening to the vagina.

In another embodiment, the present invention is directed to a method for manufacturing a personal care product of the present invention, comprising: melting together the natural glycerides at a temperature of between about 37° C. and about 80° C.; adding sodium hyaluronate and sea buckthorn powder to the melted glycerides mixture to form the personal care product; rotating the mixture at about 80° C.; filling the formulation in a product configuration; and cooling the product configuration to form a soft paste product. In another embodiment, the rotating is performed in a mechanical rotating device. In another embodiment, the product configuration is a dosage container. In another embodiment, the product configuration is a tube. In another embodiment, a mill is used to grind powders to small partial size.

In yet another embodiment, the present invention is direct to a personal care product comprising from about 72 wt. % to about 78 wt. % plant-based glycerides; from about 35 wt. % to about 37 wt. % sucrose; and from about 0.05 wt. % to about 0.15 wt. % witch hazel extract and from about 0.05 wt. % to about 0.15 wt. % *calendula*. In yet another embodiment, the present invention is direct to a personal care product comprising from about 55 wt. % to about 60 wt. % plant-based glycerides; from about 37 wt. % to about 39 wt. % sucrose; and from about 0.1 wt. % to about 0.4 wt. % hyaluronic acid and from about 0.1 wt. % to about 0.4 wt. % sea buckthorn powder. The composition is substantially free from added water or alcohol. In another embodiment, the personal care product contains less than about 5 wt. % added water or alcohol. In another embodiment, the personal care product is substantially free of synthetic chemical, a synthetic anti-microbial agent, synthetic preservative, or a synthetic hormone. In another embodiment, the plant-based glycerides comprises from about 37 wt. % to about 39 wt. % coco butter and from about 35 wt. % to about 37 wt. % kokum butter. In another embodiment, the plant-based glycerides comprises from about 28 wt. % to about 31 wt. % coco butter and from about 27 wt. % to about 29 wt. % kokum butter. In another embodiment, the personal care product has a pH from about 3.8 to about 5 in an aqueous environment, and preferably from about 3.5 to about 4.5. In another embodiment, the personal care product is in a form of cream. In another embodiment, the personal care product is in a form of a vaginal suppository. In another embodiment, the vaginal suppository melts between about 30° C. to about 37° C. In another embodiment, a mill is used to grind powders to small partial size. In another embodiment, a mill is used to grind sucrose for the personal care product.

In yet another embodiment, the present invention is directed to a method for manufacturing a personal care formulation comprising: melting together the natural glycerides at a temperature of between about 37° C. and about 80° C.; adding sucrose, witch hazel extract or hyaluronic acid to the melted glycerides mixture to form the personal care formulation; rotating the mixture at about 80° C.; filling the formulation in a product configuration; and cooling the product configuration to form in a soft paste product. In another embodiment, the rotating is performed in a mechanical rotating device. In another embodiment, the product configuration is a dosage container. In another embodiment, the product configuration is a suppository shell.

DESCRIPTION OF EMBODIMENTS OF THE INVENTION

The present invention relates to a personal care product for alleviating skin dryness. In general, the personal care product promotes healthy skin, especially skin in sensitive areas such as the vulva, breasts, face, and vaginal tract. In particular, the personal care product of the present invention is an all-natural product devoid of any artificial synthetic chemicals or synthetic hormones, and free of added alcohol or water. Embodiments of the present invention include greater than about 55 wt. % plant-based glyceride. The invention utilizes natural substances that provide an acidic pH when mixed in an aqueous environment or applied on the skin. Still further, the present invention achieves an unexpected safety level when used by women with a compromised vaginal tract. These natural products and their lipophilicity and pH optimizing effect on sensitive skin and mucous membranes of women are novel and have benefits not achieved by existing products. In a clinical trial using this formulation in women who had undergone the devastating side effects of irradiation of the genitalia, the present invention was reported to be efficacious, with high safety levels, when compared to standard of care of using traditional lubricants.

As used herein, the term formulation refers to the prepared personal care product and the terms are generally used interchangeably.

All percentages refer to weight percent (wt. %) of the component in the final product, i.e. the weight of the component as compared to the total product weight. Weight percentages are subject to precision and rounding and thus, in general, there is some variability in exact measures of weight percent, as would be readily recognized by persons skilled in the art.

As used herein, plant glycerides refers to a plant extract of fatty acid glycerides that may include monoglycerides, diglycerides and triglycerides. In diglycerides and triglycerides, the fatty acids may be the same or different. Typical plant glycerides contain a mixture of glycerides with different fatty acids. However, the composition of glycerides from a particular plant extracted in a particular way provides a relatively consistent fatty acid content. Specific plant glycerides from various sources and in various forms are well known in the art.

As will be appreciated, because the personal care product of the invention is non-aqueous, it does not have a readily quantifiable pH. Accordingly, references to pH in the present specification refer to the pH of the product in an aqueous environment. Because the skin contains some water, the pH described can be considered the pH obtained when the personal care product of the invention is applied to the skin.

An embodiment of the invention relates to a personal care product that may include natural ingredients, such as plant-based glycerides, sodium hyaluronate, and sea buckthorn powder. Another embodiment of the invention relates to a personal care product that may include natural ingredients, such as plant-based glycerides, sodium hyaluronate or witch hazel extract, and sucrose.

As used herein, the term hyaluronic acid refers not only to the acid, but also to salts such as sodium hyaluronate, and the terms are used interchangeably. Unless specified otherwise, sodium hyaluronate can be can be replaced with other hyaluronic acid salts such as potassium hyaluronate and the like. In general, hyaluronic acid and hyaluronate salts can be used interchangeably in products and formulations of the invention, unless stated otherwise. Persons skilled in the art will be able to identify appropriate forms of hyaluronic acid. The hyaluronic acid used in the present invention can be obtained from a natural source or a synthetic bioidentical hyaluronic acid that is indistinguishable from naturally occurring hyaluronic acid.

Plant-based glycerides are extracted from plants. These glycerides can be mainly derived from fatty acids such as palmitic acid, stearic acid, linoleic acid, linolenic acid, arachidic acid, oleic acid, and others, esterified onto glycerol to form the glycerides. The plant-based glycerides can be in the form of a butter (solid at room temperature), a paste (semi-solid or cream-like at room temperature), or an oil (liquid at room temperature). Their physical properties depend on the specific composition of the glycerides. Examples of plant-based glycerides include extracts of shea, cocoa, kokum, mango, palm, sunflower, walnut, avocado, and almond, many of which may be in the form of a butter, paste or oil. These products are known and have their generally meaning as understood in the art. In some embodiments, the plant-based glycerides are deodorized.

While the present invention has been described as containing cocoa butter, kokum butter and shea olein, it will be appreciated that one or more of these specific glycerides may be replaced by a plant glyceride of different origin. If a different plant glyceride is used, it should have similar physical properties, in particular, similar consistency and behavior, and provide additional properties consistent with the teachings of this specification.

According to the invention, the combination of plant-based glycerides is selected to achieve a consistency that liquefies or melts "instantly" upon application to the skin. For example, the personal care product can be in the form of a solid or cream that, on contact with skin (including mucous membranes of the vulva), it melts from the solid or highly viscous state to a free-flowing liquid state. As used herein, melting instantly means that the product liquefies on contact with the skin within, for example, five seconds, or three seconds, or two seconds or less. In the case of a solid formulation, for example a suppository, instantly melting or liquefying on contact with the skin means that the skin contacting surface of the solid melts within, for example, five seconds, or three seconds, or two seconds or less. Thus, while the formulation may remain partially solid, the surface melts on contact. The remainder of the solid formulation may melt over some extended time frame, for example within 15 minutes, within ten minutes, or within 5-10 minutes.

Embodiments of the invention may include cocoa butter, an edible vegetable fat extracted from the cocoa bean. Cocoa butter has a cocoa flavor and aroma. Its melting point is just below human body temperature. Cocoa butter contains between 57-64% saturated fats and 36-43% unsaturated fats. Embodiments of the invention include from about 20 wt. % to about 45 wt. % cocoa butter, from about 27 wt. % to about 34 wt. % cocoa butter, from about 24 wt. % to about 34 wt. % cocoa butter; or from about 32 to about 45 wt. %. Some embodiments of the invention include from about 28 wt. % to about 31 wt. % cocoa butter; from about 30 wt. % to about 32 wt. %; or from about 37 wt. % to about 39 wt. %.

Embodiments of the invention may include kokum butter. Kokum butter is extracted from the seeds of the kokum tree. Kokum butter contains up to 60-65% saturated fatty acid and is a solid in room temperature. Embodiments of the invention include from about 8 wt. % to about 45 wt. % kokum butter. Some embodiments contain from about 11 wt. % to about 16 wt. % kokum butter, for example from about 14 wt. % to about 16 wt. % kokum butter. Embodiments can contain from about 23 wt. % to about 33 wt. % kokum butter, for example, from about 27 wt. % to about 29 wt. % kokum butter. Still other embodiments contain from about 30 wt. % to about 45 wt. % kokum butter, or from about 35 wt. % to about 37 wt. % kokum butter.

Embodiments of the invention may include shea olein. Shea olein is an off-white or ivory-colored natural glyceride extracted from the nuts of shea trees. Shea olein melts at body temperature and it is absorbed rapidly into the skin. In embodiments of the present invention containing shea olein, the personal care product has the consistency of a paste. Embodiments of the invention include from about 35 wt. % to about 60 wt. % shea olein, from about 40 wt. % to about 55 wt. % shea olein or from about 45 wt. % to about 51 wt. % shea olein. Some embodiments of the invention include from about 49 wt. % to about 51 wt. % shea olein.

Other embodiments of the invention is substantially free of shea olein in the personal care product. Embodiments without shea olein are generally in the form of a solid. Such embodiments include at least about 38 wt. % total plant-based glyceride. In such embodiments, the personal care product includes at least about 38 wt. % plant-based glyceride, at least about 40 wt. % plant-based glyceride, or at least about 47 wt. % plant-based glyceride. Embodiments of the invention includes from about 20 wt. % to about 45 wt. % cocoa butter, at least from about 22 wt. % to about 40 wt. % cocoa butter, or at least about 24 wt. % to about 34 wt. % cocoa butter. Some embodiments of the invention include from about 28 wt. % to about 32 wt. % cocoa butter. Embodiments of the invention include from about 14 wt. % to about 40 wt. % kokum butter, from about 20 wt. % to about 36 wt. % kokum butter, or from about 23 wt. % to about 33 wt. % kokum butter. Some embodiments of the invention include from about 14 wt. % to about 29 wt. % kokum butter.

Water and alcohols are dehydrating to skin membranes due to the concentration gradient of salts and sugars in intracellular fluids. Embodiments of the invention relate to a personal care product that is substantially free of added water or alcohols, including diols and polyols. For example, substantially free can mean that the personal care product has less than about 5 wt. % of added water or alcohols, less than about 4 wt. % of added water or alcohols, less than about 3 wt. % of added water or alcohols, less than about 2 wt. % of added water or alcohols, less than about 1 wt. % added water or alcohols, less than about 0.5 wt. % added water or alcohols, less than about 0.1 wt. % added water or alcohols, or less than about 0.05 wt. % added water or alcohols. For example, the personal care product is substantially free of methanol, ethanol, propanol, and other monohydric alcohols; ethylene glycol, propylene glycol, and other diols; and glycerol (glycerin), and other polyols. In exemplary embodiments, the personal care product is substantially free of added water or alcohols. In exemplary embodiments, the personal care product contains no added water or alcohols.

Embodiments of the invention relate to personal care products are substantially free of synthetic chemicals, such as synthetic preservatives, anti-microbial agents, or chemical stabilizers. Synthetic chemicals exclude materials that are synthesized and indistinguishable from the corresponding bio-generated or natural material in all respects. In other words synthetic bio-identical materials are not considered to be synthetic chemicals. Examples of synthetic preservatives, antimicrobial agents, and chemical stabilizers include benzoates (e.g., benzoic acid and sodium benzoate), hydroxybenzoate and derivatives, sorbates (e.g., sorbic acid and sodium sorbate), proprinates, nitrates, nitrite, sulfites (sulfur dioxide, sodium bisulfite), chelating agents, propyl gallate, gallic acid, sodium gallate, methyl paraben, propyl paraben, butyl paraben, ethyl paraben, quaternium-15, formaldehyde, lactic acid, propionic acid, sodium propionate, ascorbic acid, sodium ascorbate, butylated hydroxytoluene, butylated hydroxyanisole, and tocopherols. For example, the personal care product has less than about 5 wt. % of added synthetic chemicals, less than about 4 wt. % added synthetic chemicals, less than about 3 wt. % added synthetic chemicals, less than about 2 wt. % of added synthetic chemicals, less than about 1 wt. % added synthetic chemicals, less than about 0.5 wt. % added synthetic chemicals, less than about 0.1 wt. % added synthetic chemicals, or less than about 0.05 wt. % added synthetic chemicals. For example, the personal care product has less than about 5 wt. % of added synthetic preservatives or anti-microbial agents, less than about 4 wt. % added synthetic anti-microbial agents, less than about 3 wt. % added synthetic anti-microbial agents, less than about 2 wt. % of added synthetic preservatives or anti-microbial agents, less than about 1 wt. % added synthetic preservatives or anti-microbial agents, less than about 0.5 wt. % added synthetic anti-microbial agents, less than about 0.1 wt. % added synthetic anti-microbial agents, or less than about 0.05 wt. % added synthetic preservatives or anti-microbial agents. For example, the personal care product has less than about 5 wt. % of added chemical stabilizers, less than about 4 wt. % added chemical stabilizers, less than about 3 wt. % added chemical stabilizers, less than about 2 wt. % of added chemical stabilizers, less than about 1 wt. % added chemical stabilizers, less than about 0.5 wt. % added chemical stabilizers, less than about 0.1 wt. % added chemical stabilizers, or less than about 0.05 wt. % added chemical stabilizers. In exemplary embodiments, the personal care product is substantially free of no added synthetic chemicals, such as synthetic preservatives, anti-microbial agents, or chemical stabilizers. In exemplary embodiments, the personal care product contains no added synthetic chemicals, such as synthetic preservatives, anti-microbial agents, or chemical stabilizers.

Hyaluronic acid is a non-sulfated glycosaminoglycan, naturally found in the body and is the main component of the extra cellular matrix. Hyaluronic acid is found in high levels in the skin, where it is naturally produced by both fibroblasts and keratinocytes and exists as a polymer of medium molecular weight (600-1,000 kDa). An important function of hyaluronic acid is to hold water in the intercellular matrix of the connective tissue. This water-binding capacity significantly contributes to the elasticity of the skin, serving as a water reservoir. With aging, the quantity and quality of hyaluronic acid in the skin decreases, leading to skin dryness.

Embodiments of the invention may include hyaluronic acid or its derivatives. Hyaluronic acid is a skin hydrating agent that can help restore water to dehydrated skin. When applied according to a method of the invention, hyaluronic acid molecules can deliver substantially instant hydration to the skin. As used herein, the term hyaluronic acid refers not only to the acid, but also to salts such as sodium hyaluronate. Similarly, unless specified otherwise, sodium hyaluronate can be replaced with other hyaluronic acid salts such as potassium hyaluronate and the like. In general, hyaluronic acid and hyaluronate salts can be used interchangeably in products and formulations of the invention, unless stated otherwise. Persons skilled in the art will be able to identify appropriate forms of hyaluronic acid.

The hyaluronic acid used in the invention generally has a very low molecular weight, e.g. about 100 kDa or less, about 50 kDa or less, or about 5 kDa. This low molecular weight allows for increased permeation through the skin compared to high molecular weight hyaluronic acid. The hyaluronic acid can rejuvenate the skin by improving its viscoelastic properties and significantly decreases deep wrinkles. Hyaluronic acid is commercially available from a number of sources. Embodiments of the invention include about 0.0001 wt. % to about 3 wt. % hyaluronic acid, about 0.005 wt. % to about 0.5 wt. % hyaluronic acid, or about 0.05 wt. % to about 1.5 wt. % hyaluronic acid. Some embodiments of the invention include about 0.05 wt. % to about 1.5 wt. % hyaluronic acid.

Embodiments of the invention may include sea buckthorn powder or extract of sea buckthorn (Hippophae). In some embodiments, sea buckthorn oil extracted from sea buckthorn berries may be used. Sea buckthorn oil, either taken orally or applied topically, is believed to be a skin softener. It has also been reported that sea buckthorn oil is effective for alleviating dry mucous membranes, such as eyes and mouth. Furthermore, sea buckthorn powder contains omega-7 fatty acid and when dissolved in a mixture, it generates an acidic pH in the mixture. A user suffering from bacterial vaginosis, trichomoniasis, and atrophic vaginitis generally has a vaginal pH of 4.5 or higher. The acidic nature of the sea buckthorn may restore the pH level of the vaginal area to a pH of 3.5 to 4.5, for example around 3.7, thus creating an environment where the virginal flora may be restored. Embodiments of the invention include about 0.0001 wt. % to about 3 wt. % sea buckthorn powder, about 0.005 wt. % to about 2 wt. % sea buckthorn powder, or about 0.05 wt. % to about 1.5 wt. % sea buckthorn powder. Some embodiments of the invention include about 0.05 wt. % to about 1.5 wt. % sea buckthorn powder.

Embodiments of the invention include Vitamin E. Vitamin E is a natural preservative, which protects lipids and prevents the oxidation of polyunsaturated fatty acids. Embodiments of the invention include about 0.1 wt. % to about 10 wt. % Vitamin E, about 1 wt. % to about 8 wt. % Vitamin E, or about 3 wt. % to about 5 wt. % Vitamin E. Some embodiments of the invention include about 3 wt. % to about 5 wt. % Vitamin E. Other natural preservatives may also be used.

Embodiments of the invention may include menthol. Natural menthol may be extracted from corn mint, peppermint, or other mint oil. Menthol may be used to provide a cooling sensation on the skin. Other skin cooling oils may also be used. Embodiments of the invention include about 0.5 wt. % to about 3 wt. % menthol, about 0.1 wt. % to about 3 wt. % menthol, or about 0.05 wt. % to about 2 wt. % menthol. Some embodiments of the invention include about 1 wt. % to about 1.5 wt. % menthol.

Some embodiments of the invention may include witch hazel powder or extract (*Hammamelis virginiana*) as a substitute for hyaluronic acid. Witch hazel powder is from flowering plants in the family of Hamamelidaceae. Witch hazel is a strong anti-oxidant and astringent and may be a powder or an oil. Witch hazel can be added as the extract or, in some embodiments, as a homeopathic solution prepared according to methods disclosed in the Homeopathic Pharmacopeia of the United States (HPUS). For example, the witch hazel can be added as a 6×HPUS solution. Embodiments of the invention include about 0.0001 wt. % to about 1 wt. % witch hazel, about 0.005 wt. % to about 0.5 wt. % witch hazel or its homeopathic solution, or about 0.05 wt. % to about 0.15 wt. % witch hazel or its homeopathic solution. Preferably, embodiments of the invention include about 0.05 wt. % to about 0.15 wt. % witch hazel. Other preferred embodiments of the invention include about 0.05 wt. % to about 0.15 wt. % witch hazel as a 6× homeopathic solution.

Some embodiments of the invention may include *calendula*, which as referred to herein is an extract of *Calendula* sp., such as *Calendula officinalis*. *Calendula* can be added as the extract or, in some embodiments, as a homeopathic solution, for example, the *calendula* can be added as a 1×HPUS solution. Embodiments of the invention include about from 0.0001 wt. % to about 1 wt. % *calendula* or its homeopathic solution, from to about 0.005 wt. % to about 0.5 wt. % *calendula* or its homeopathic solution, or from about 0.05 wt. % to about 0.15 wt. % *calendula* or its homeopathic solution. Preferably, embodiments of the invention include about 0.05 wt. % to about 0.15 wt. % *calendula*. Other preferred embodiments include about 0.05 wt. % to about 0.15 wt. % *calendula* as a homeopathic solution Another embodiment of the invention relates to a personal care product that includes sucrose and a natural fragrance in a solid formulation for use as a suppository, which lubricates and protects the vaginal mucosal membranes. When used as a suppository ovule form, the personal care product melts completely between 5 to 10 minutes. The suppository contains sufficient oil for coating the vaginal tract, allowing the user to receive the maximum benefit of the personal care product. Topical sucrose stabilizes plant oil at room temperature, and upon melting at body temperature may serve as a topical antibiotic as shown by scientific studies. Accordingly, topical sucrose, e.g. sucrose alone or as part of a formulation for application to the skin or vulva, including the vaginal tract, can function as an antibiotic to pathogenic bacteria, thereby facilitating the restoration of healthy bacterial flora, for example in the in vagina.

Sucrose is a natural preservative, which protects lipids and prevents the oxidation of polyunsaturated fatty acids. Surprisingly and unexpectedly, it has been found that when used topically, sucrose can restore the vaginal flora. In addition, topical sucrose is antibacterial and may inhibit the development of vaginal infection with users undergoing perimenopause or menopause. As used in the specification, sucrose also functions as a temperature control agent for the composition by keeping the composition in its solid form. When the personal care product (a suppository) is inserted into the body, the body temperature slowly melts the suppository and the composition is distributed in the vagina, for example, the suppository may melt from between 5 to 10 minutes. Embodiments of the invention may include about 25 wt. % to about 50 wt. % sucrose, about 20 wt. % to about 42 wt. %, about 28 wt. % to about 45 wt. % sucrose, or about 32 wt. % to about 42 wt. % sucrose. Some embodiments of the invention include about 36 wt. % to about 38 wt. % sucrose.

Another embodiment of the invention relates to a personal care product that includes a natural fragrance, in particular, natural fragrances that provide a soothing effect by adding an aromatherapy aspect to the formulation. Natural fragrances include, for example, lavender oil and citrus extracts. Embodiments of the invention include about 0.5 wt. % to about 5 wt. % natural fragrance oil, about 0.1 wt. % to about 3 wt. % natural fragrance oil, or about 0.05 wt. % to about 1.5 wt. % natural fragrance oil. Some embodiments of the invention include about 0.05 wt. % to about 0.15 wt. % natural fragrance oil. The natural fragrance oil may be selected from the group consisting of lavender oil, sandalwood oil, jasmine oil, vanilla oil, gardenia oil, rose oil, and citrus oil. In particular, personal care products of the invention in the form of suppositories contain a natural fragrance oil.

Another embodiment of the invention relates to a personal care product that may be used to alleviate vulval dryness, including dryness of vaginal lips (labia majora and labia minora), clitoris, vulval vestibule, urinary meatus, vestibular glands and/or the opening to the vagina.

The combination of ingredients, in particular the combination of plant butters and hyaluronic acid, are selected to achieve an optimal pH for the particular application. When mixed with an aqueous environment, personal care compositions of the invention can have a pH ranging from about 3.5 to about 5.5. For example, in embodiments for use as a topical skin creams, the pH can be comparable to that of skin, for example in the range of about 4-6. In preferred embodiments, the personal care products of the invention provide a pH of about 5.5 when applied to the skin in order to contribute to and maintain the optimal skin pH. In other embodiments of the invention related to a personal care product for use in the labial area, the pH can be in the range of about 5.0-5.5, the optimal pH of the labia. In embodiments, the pH can be about 5.2. In other embodiments of the invention related to a personal care product for use in the vagina or vaginal area, the pH can be in the range of about 3.5-4.5, the optimal pH of the vagina. In embodiments, the pH can be about 3.7. When the pH of the vaginal tract shifts from acidic to neutral during perimenopause and menopause, it allows pathogenic bacteria to replace the natural flora, resulting in recurring infections such as bacterial vaginosis. Returning the pH to pre-menopausal acidic levels on the surface of the vaginal tract can promote healthy bacterial flora and reduce bacterial vaginosis.

Another embodiment of the invention relates to a personal care product in the form of cream.

Another embodiment of the invention relates to a personal care product in the form of a vaginal suppository.

Embodiments of the invention relate to a personal care product, in the form of a solid, a vaginal suppository or cream that melts at a temperature between about 30° C. and about 37° C., or between about 33° C. and about 37° C.

In an embodiment, a formulation for alleviating vulval or labial dryness may include natural ingredients, such as, from about 45 wt. % to about 51 wt. % shea olein; from about 27 wt. % to about 34 wt. % cocoa butter; from about 11 wt. % to about 16 wt. % kokum butter; from about 0.05 wt. % to about 0.15 wt. % sodium hyaluronate; and from about 0.05 wt. % to about 1.5 wt. % sea buckthorn powder.

Embodiments of the invention relate to a method for alleviating vulval dryness, wherein the formulation is effective for retaining moisture in vaginal lips (labia majora and labia minora), clitoris, vulval vestibule, urinary meatus, vestibular glands and the opening to the vagina.

Embodiments of the invention relate to a method for manufacturing a personal care formulation in the form of a vaginal suppository. The method includes the steps of: mixing and melting together the plant-based triglycerides at an elevated temperature, adding to the mixture hyaluronic acid, sea buckthorn powder, natural oil, and/or dry ingredients, and rotating the mixture while cooling for a period of time. For example, the method may include: mixing together sucrose from 20 wt. % to 42 wt. %; cocoa butter from 24 wt. % to 45 wt. %; kokum butter from 23 wt. % to 45 wt. %; rotating the mixture while cooling from above 38° C. to below 33° C. for between 2 and 120 minutes.

Embodiments of the invention relate to a method for manufacturing a personal care formulation in the form of a vaginal suppository. The method includes the steps of: mixing and melting together the plant-based triglycerides at an elevated temperature, adding to the mixture witch hazel, *calendula*, natural oil, and/or dry ingredients, and rotating the mixture while cooling for a period of time. For example, the method may include: mixing together sucrose from 20 wt. % to 42 wt. %; cocoa butter from 24 wt. % to 45 wt. %; kokum butter from 23 wt. % to 45 wt. %; rotating the mixture while cooling from above 38° C. to below 33° C. for between 2 and 120 minutes.

Embodiments of the invention relate to a method for manufacturing a personal care formulation, which can also include melting the formulation between a temperature of about 37° C. to about 80° C. for between 5 and 15 minutes, filling a product configuration, such as a mold, with the formulation and cooling to about −20° C. for a period of more than 15 minutes.

Embodiments of the invention relate to a method for manufacturing a personal care formulation, wherein a mill is used to grind powders to small partial size. In another embodiment, a mill is used to grind sucrose for the personal care formulation to form a vaginal suppository.

The following manufacturing procedure may be used to manufacture personal care products according to the invention that are in the form of a cream.

Plant-based glycerides (for example, cocoa butter, kokum butter, and shea olein) are combined and heated to about 80° C. The dry powdered ingredients (for example, sea buckthorn powder) are slowly combined and added to the warmed butter mixture. Other ingredients, such as fragrance or menthol are also added to the mixture. The mixture is stirred for 25 minutes at 80° C. or until homogeneous. The mixture is then injected into molds or dosage containers and cooled rapidly to 4° C. while rotating in the molds/containers to result in soft yellow paste.

Embodiments of the invention relate to using pharmaceutical grade ingredients, manufacturing under good manufacturing practice, and testing final product for levels of heavy metals below 0.1 ppm, yeast and mold less than 10 cfu/g, and negative detection for *E. Coli, salmonella, Staphylococcus aureus* and *Pseudomonas aeruginosa*.

EXAMPLES

Example 1—Labial Cream

A labial cream formulation for alleviating dryness can be formulated as follows:

| Ingredient | Possible Range (wt. %) | Exemplary Range (wt. %) |
|---|---|---|
| Cocoa Butter | 27-34 | 30-32 |
| Kokum Butter | 11-16 | 14-16 |
| Vitamin E | 3-5 | 3-5 |
| Hyaluronic acid (Sodium Hyaluronate) | 0.05-0.15 | 0.05-0.15 |
| Sea buckthorn powder | 0.05-1.5 | 0.05-0.15 |
| Shea olein | 45-51 | 49-51 |
| Total | 100 | 100 |

Example 2—Body Cream

A body cream formulation for alleviating dryness and soothing pain and discomfort can be formulated as follows:

| Ingredient | Possible Range (wt. %) | Exemplary Range (wt. %) |
|---|---|---|
| Cocoa Butter | 27-34 | 30-32 |
| Kokum Butter | 11-16 | 14-16 |
| Vitamin E | 3-5 | 3-5 |
| Hyaluronic acid (Sodium Hyaluronate) | 0.05-0.15 | 0.05-0.15 |
| Sea buckthorn powder | 0.05-1.5 | 0.05-0.15 |
| Shea olein | 45-51 | 49-51 |
| Menthol | 0.05-2 | 1-1.5 |
| Total | 100 | 100 |

Example 3a—Vaginal Suppository

A vaginal suppository formulation for alleviating dryness can be formulated as follows:

| Ingredient | Possible Range (wt. %) Broad Range | Exemplary Range (wt. %) Preferred/Commercial Range |
|---|---|---|
| Cocoa Butter | 24-34 | 28-31 |
| Kokum Butter | 23-33 | 27-29 |
| Vitamin E | 3-5 | 3-5 |
| Sucrose | 32-42 | 37-39 |
| Hyaluronic acid (Sodium Hyaluronate) | 0.05-1.5 | 0.1-0.4 |
| Sea buckthorn powder | 0.05-1.5 | 0.1-0.4 |
| Total | 100 | 100 |

Example 3b—Vaginal Suppository

Another vaginal suppository formulation for alleviating dryness can be formulated as follows:

| Ingredient | Possible Range (wt. %) Broad Range | Exemplary Range (wt. %) Preferred/Commercial Range |
|---|---|---|
| Cocoa Butter | 32-45 | 37-39 |
| Kokum Butter | 30-45 | 35-37 |
| Sucrose | 20-35 | 26-28 |
| Hammamelis Virginiana (witch hazel) | 0.05-1.5 | 0.05-0.15 |
| Calendula | 0.015-1.5 | 0.05-0.15 |
| Total | 100 | 100 |

Example 4—Clinical Results of Vaginal Suppositories

Objective

Vaginal moisturizer containing hyaluronic acid are indicated for menopausal vaginal dryness. The objective was to conduct a pilot to evaluate whether a completely natural vaginal moisturizer containing hyaluronic acid is safe and effective in women with severely compromised vaginal health due to radiation therapy to treat gynecologic cancer. A secondary object was to identify whether the natural vaginal moisturizer could be used with a dilator.

Background

Cancer of the vulva, vagina, uterine cervix and uterine corpus is routinely treated with external beam radiation and brachytherapy. Treatment methods often cause short-term inflammation, bleeding, soreness and irritation and long-term vaginal scarring and stenosis (narrowing). In extreme cases, the vaginal wall can fuse together and scar shut. Cancer patients are counselled to utilize a dilator (glass, plastic or rubber) to prevent the vaginal wall from becoming narrower and shorter. The vaginal tissue also becomes drier and less elastic, particularly if pelvic radiation has damaged the ovaries and induced menopause.

Up to 30% of young women receiving alkylating therapy and pelvic radiation have acute ovarian failure and therefore medically-induced early menopause. Many gynecological cancer patients are facing both induced menopause and cancer treatment at the same time, with accompanying psychological and physical distress. In addition, intercourse for gynecologic patients is often painful, a condition which can be long-lasting due to the long-term effects of radiation therapy.

Due to the long-lasting effects of radiation therapy, dilator usage is recommended indefinitely. The use of a dilator is often accompanied with an alcoholic gel that increases dryness. Therefore, a non-alcohol based product is desirable for this patient population to 1) promote efficacy in treating symptoms of vaginal dryness, 2) prevent stenosis when used in combination with a dilator, and 3) prevent dryness associated with using an alcohol-based gel.

This example demonstrates the potential usage modalities and addresses safety issues in this severely compromised patient population before undertaking a larger clinical trial.

Design

This non-interventional, open-label pilot trial was conducted at the BC Cancer Agency in British Columbia, Canada. The information was collected by survey in women treated for gynecologic cancer receiving irradiation. Women were provided with samples of natural vaginal moisturizer and asked to complete a survey after usage. Women were informed that they could use the vaginal moisturizer in advance of intercourse, with a dilator and/or for general vaginal comfort. The survey results were reviewed with a radiation oncologist during a follow-up meeting.

Sample survey questions include: Are you using a vaginal dilator after radiation therapy? If yes, how many times a week? How are you using the suppository moisturizer? Answers include: (1) alone, without a dilator, for general comfort; (2) prior to intercourse; (3) after intercourse); (4) with a dilator, occasionally; (5) with a dilator, every time or almost every time; or (6) other.

Women used a 100% natural vaginal suppository that contains hyaluronic acid and is pH balanced to 3.7. Other suppository ingredients include cocoa butter, mangosteen (kokum) butter, sea buckthorn extract, vitamin E, and sucrose. Hyaluronic acid has been used in a clinical trials to improve symptoms of vaginal atrophy.

Women were advised to use the suppository at their own discretion and without clinical intervention in order to better understand usage modalities. Any adverse events were self-recorded and followed up with a radiation oncologist.

Results

The results of a pilot non-interventional, open-label study of use of a completely natural plant-based vaginal moisturizer in eight women who have received gynecologic radiation therapy in British Columbia, Canada, and were under the care of an oncologist were summarized. Out of eight women, seven completed a survey and utilized the suppository of the present invention. One women did not use the suppository because she found the suppository shell difficult to open.

The results of the trial indicate that all women who used the vaginal moisturizer found at least one benefit of decrease in vaginal discomfort, improvement in intercourse comfort, improvement in ease of dilator insertion and increase in vaginal health and well-being.

TABLE 1

Benefits of Suppository (moisturizer).

| Benefits | Patient No. | | | | | | |
|---|---|---|---|---|---|---|---|
| | 1 | 2 | 3 | 4 | 5 | 6 | 7 |
| Decreases general vaginal discomfort, e.g. itchiness or dryness | X | | x | x | x | | |
| Improves intercourse comfort | X | x | x | x | | x | x |
| Improves ease of dilator insertion | X | | x | x | | | |
| Increases vaginal health and well-being | x | | x | x | | | x |

Four women found two or more benefits, three women benefitted in all areas (discomfort, intercourse, dilator usage and well-being), one woman found improved comfort with intercourse solely and another women experienced decreased discomfort solely.

Out of seven women surveyed, six indicated they would use the natural vaginal moisturizer again and one was unsure. Three of seven women were also using another vaginal product at the same time. The one women who indicated "not sure" still received benefit, however, she was also using another product and had discomfort, not described nor elaborated.

Women were using the vaginal moisturizer for different and multiple purposes. Six out of the seven were using the vaginal moisturizer for intercourse, one women for both intercourse and dilator usage, one women for general comfort and one woman used the vaginal moisturizer only with a dilator.

TABLE 2

Usage Modalities

| Usage Modality | Patient No. | | | | | | |
|---|---|---|---|---|---|---|---|
| | 1 | 2 | 3 | 4 | 5 | 6 | 7 |
| Alone, without a dilator, for general comfort | | | | | x | | |
| Prior to intercourse | x | x | | x | | x | x |
| After intercourse | | | | | | | |
| With a dilator, occasionally | | | | | | | x |
| With a dilator, every time or almost every time | | | x | | | | |
| Other | | | | | | | |

Dosage schedules varied significantly between women. Two women used the vaginal moisturizer less than once a month, three used it 1 to 4 times a month, one used it 5 to 8 times monthly and another woman used the product 9 to 15 times in a one month period.

The product is an ovule formed of plant butters. Women open and peel a plastic suppository shell, remove the ovule, and insert the suppository moisturizer using fingers. Most women (five) rated the insertion as easy, one considered it mildly difficult and one found the application moderately difficult.

CONCLUSION

No adverse events were reported with usage of the natural vaginal moisturizer. Despite the small sample number, it is concluded that a natural vaginal moisturizer appears to be safe and may be shown to provide benefit to women who have received radiation therapy after gynecologic cancer. The vaginal moisturizer may also be utilized in conjunction with a dilator. Dilator usage helps prevent vaginal closure due to scarring after radiation therapy.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever.

We claim:

1. A personal care product, comprising, based on the total weight of the personal care product:
   at least 55 wt. % plant-based glycerides;
   from about 20 wt. % to about 42 wt. % sucrose; and
   from about 0.005 wt. % to about 0.15 wt. % witch hazel extract;
   substantially free of added water or alcohol.

2. The personal care product of claim 1, comprising, based on the total weight of the personal care product, from about 72 wt. % to about 76 wt. % of the plant-base glycerides; from about 26 wt. % to about 28 wt. % of the sucrose; from about 0.005 wt. % to about 0.15 wt. % of the witch hazel extract; and optionally further comprising from about 0.05 wt. % to about 0.15 wt. % *calendula*.

3. The personal care product of claim 2, wherein, based on the total weight of the personal care product, the plant-based glycerides comprise from about 32 wt. % to about 45 wt. % cocoa butter and from about 30 wt. % to about 45 wt. % kokum butter.

4. The personal care product of claim 3, wherein, based on the total weight of the personal care product, the plant-based glycerides comprise from about 37 wt. % to about 39 wt. % of the cocoa butter and from about 35 wt. % to about 37 wt. % of the kokum butter.

5. The personal care product of claim 1, wherein the personal care product has less than about 5 wt. % of added water or alcohol.

6. The personal care product of claim 1, wherein the personal care product is substantially free of synthetic chemical, synthetic anti-microbial agent, synthetic preservative, or a synthetic hormone.

7. The personal care product of claim 1, wherein the plant-based glycerides comprise cocoa butter and kokum butter.

8. The personal care product of claim 1, wherein the plant-based glyceride is deodorized.

9. The personal care product of claim 1, wherein the personal care product has a pH from about 3.5 to about 4.5 in an aqueous environment.

10. The personal care product of claim 1, wherein the personal care product is in a form of a vaginal suppository.

11. The personal care product of claim 10, wherein the vaginal suppository melts between 30° C. and 37° C.

12. A method for retaining moisture, comprising applying onto dry skin the personal care product according to claim 1.

13. The method of claim 12, wherein the personal care product is effective for retaining moisture in at least one of vaginal lips (labia majora and labia minora), clitoris, vulval vestibule, urinary meatus, vestibular glands, and vaginal opening.

14. The personal care product according to claim 1, wherein the product is made by a process comprising the steps of:
   melting together the plant-based glycerides at a temperature of between about 37° C. and about 80° C.;
   adding sucrose and witch hazel extract to the melted plant-based glycerides mixture to form a personal care formulation;
   rotating the formulation at about 80° C.;
   filling the formulation in a product configuration; and
   cooling the product configuration to form the personal care product.

15. The personal care product of claim 14, wherein the rotating is performed in a mechanical rotating device.

16. The personal care product of claim 14, wherein the product configuration is a dosage container.

17. The personal care product of claim 14, wherein the product configuration is a suppository shell.

* * * * *